(12) United States Patent
Yabe et al.

(10) Patent No.: US 6,623,858 B1
(45) Date of Patent: Sep. 23, 2003

(54) METAL OXIDE DOPED CERIUM OXIDES, METHOD FOR THE PREPARATION THEREOF, RESIN COMPOSITION AND COSMETIC COMPOSITION THEREWITH

(75) Inventors: Sinryo Yabe, Tokyo (JP); Kota Tofukuji, Tokyo (JP); Shigeyoshi Momose, Tokyo (JP); Sakae Yoshida, Tokyo (JP); Kazuyuki Tahira, Tokyo (JP); Tsugio Sato, Sendai (JP)

(73) Assignees: Kose Corporation, Tokyo (JP); Nippon Inorganic Colour & Chemical Co. Ltd., Tokyo (JP)

( * ) Notice: Subject to any disclaimer, the term of this patent is extended or adjusted under 35 U.S.C. 154(b) by 0 days.

(21) Appl. No.: 09/505,730

(22) Filed: Feb. 17, 2000

(30) Foreign Application Priority Data

May 25, 1999 (JP) ............................................. 11-144664

(51) Int. Cl.$^7$ ........................ B32B 15/00; B32B 27/00; A61K 7/42
(52) U.S. Cl. ...................... 428/403; 428/404; 428/407; 424/59; 524/430
(58) Field of Search ................................ 423/263, 275; 502/304, 302, 303; 524/430; 424/59, 60; 428/403, 404, 407

(56) References Cited

U.S. PATENT DOCUMENTS

| | | | | |
|---|---|---|---|---|
| 4,601,755 A | * | 7/1986 | Melard et al. | |
| 4,610,867 A | | 9/1986 | Seiyama et al. | |
| 5,326,737 A | * | 7/1994 | Kay et al. | 423/263 |
| 5,389,352 A | * | 2/1995 | Wang | 423/263 |
| 5,516,597 A | * | 5/1996 | Singh et al. | 429/30 |
| 5,688,439 A | * | 11/1997 | Chopin et al. | 252/309 |
| 5,750,090 A | * | 5/1998 | Yoshida et al. | 424/59 |
| 6,132,743 A | * | 10/2000 | Kuroda et al. | 423/622 |
| 6,197,282 B1 | * | 3/2001 | Oshima et al. | 424/59 |
| 6,204,219 B1 | * | 3/2001 | Brezny et al. | 423/263 |
| 6,214,306 B1 | * | 4/2001 | Aubert et al. | 423/212 |

FOREIGN PATENT DOCUMENTS

| | | |
|---|---|---|
| EP | 0 207 857 A | 1/1987 |
| EP | 0 517 554 A | 12/1992 |
| EP | 0 588 691 A | 3/1994 |
| EP | 0 810 181 A | 12/1997 |
| WO | 97/02213 | * 1/1997 |

OTHER PUBLICATIONS

Rajendran, M. et al., "Combustion Synthesis, Powder . . .", Journal of Materials Science, Chapman and Hall Ltd., London, GB, vol. 33, No. 20, Oct. 15, 1988, pp. 5001–5006.

* cited by examiner

Primary Examiner—Steven Bos
(74) Attorney, Agent, or Firm—Sherman & Shalloway

(57) ABSTRACT

The present invention relates to the metal oxide doped cerium oxide which has an excellent ultraviolet ray shielding effect and a transparency and whose catalytic activity is reduced. More in detail, relates to the metal oxide doped cerium oxide composed of cerium oxide in which metal ion having larger ion radius than that of $Ce^{4+}$ and/or lower valence metal ion than $Ce^{4+}$, such as $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$, $Ce^{3+}$ and so on are doped. Said metal oxide doped cerium oxide can be prepared at the temperature lower than 60° C. and in the condition of pH higher than 5 by reacting aqueous solution of cerium salt, aqueous solution of metal ion having larger ion radius than that of $Ce^{4+}$ and/or lower valence metal ion than $Ce^{4+}$ and alkali, then adding oxidizing agent. Further, said metal oxide doped cerium oxide can be blended to resin composition or cosmetic composition and can display and ultraviolet shielding effect without spoiling transparency at visible ray region.

32 Claims, 3 Drawing Sheets

METAL OXIDE DOPED CERIUM OXIDES, METHOD FOR THE PREPARATION THEREOF, RESIN COMPOSITION AND COSMETIC COMPOSITION THEREWITH

BACKGROUND OF THE INVENTION

1. Field of the Invention

The present invention relates to metal oxide doped cerium oxides and a method for the preparation thereof. Further, the present invention relates to a resin composition or a cosmetic composition in which said metal oxide doped cerium oxides or a complex composed of said metal oxide solid doped cerium oxides and an oxide are blended.

2. Description of the Prior Art

As is well known, ultra violet ray causes degradation of plastic resins, and many kinds of countermeasure are carried out to protect the degradation. As one of the countermeasure method, it is widely practiced that a plastic resin is admixed with an ultraviolet shielding agent including an organic ultra violet ray absorbing agent or an inorganic ultraviolet ray scattering agent. And by admixing these agents in plastic resin, the adverse influence of ultra violet ray is reduced. As the organic ultra violet ray absorbing agent, salicylic acid type compound, benizophenon type compound, benzotriazol type compound or cyanoacrylate type compound can be mentioned, however, recently, the lack of heat resistance, lack of durability to weather or the safety of decomposed chemicals of it are becoming serious problems. To solve these problems, fine particles of titanium dioxide or fine particles of zinc oxide which are the inorganic ultra violet ray scattering agent are developed, however, the lack of dispersability of these agents is a problem and the catalytic activity of these agent are becoming a new problem. Recently, especially regarding titanium dioxide, it is pointed out that the generation of singlet oxygen by photo catalyst function of it causes new problem.

Ultraviolet ray has an adverse influence also on living bodies. Namely, it is well-known that the so called UV-B ultraviolet ray in the wavelength range of 280 to 320 nm causes cutaneous inflammations such as erythemas blister and the like while the so called UV-A ultraviolet ray in the wavelength range 320 to 400 nm causes tanning of skin by the accelerated formation of melanin. As the countermeasure method against above mentioned adverse influences of the ultraviolet ray, many kinds of sunscreen cosmetic compositions have been developed hereto before. The ultraviolet shielding agents contained in conventional sunscreen cosmetic compositions can be grossly classified into two types including an ultraviolet absorbing agent such as cinnamic acid type, benzophenon type or dibenzoylmethane type and an ultraviolet scattering agent such as zinc oxide or titanium dioxide. However, above mentioned ultraviolet absorbing agents have several problems, such as low absorptivity of ultraviolet ray and safety when the admixing amount in a cosmetic composition is too high. Further, in a case of conventional ultraviolet scattering agent, since it is impossible to improve the transparency even if the (dispersibility of particles is improved, the admixing use of it not only causes the deterioration of feeling when the cosmetic composition is applied but also the skin look becomes unnatural. Recently, the use of cerium compound as an ultraviolet scattering agent has been proposed, for example, in Japanese Patent Laid Open Publication 6-145645 or Japanese Patent Laid Open Publication 7-207151. However, since cerium oxide has strong catalytic activity, it has a problem that accelerates the oxidation decomposition of resin or oil and causes color change and generates offensive odor when admixed in cosmetic compound or resin. Thereupon, the development, of new cerium compound which has a function as the ultraviolet scattering agent and does not have catalytic activity has been desired. And in Japanese Patent Laid Open Publication 9-118610, silica-cerium oxide composite particle is proposed, however, the reduction of catalytic activity of said silica-cerium oxide composite particle is almost accomplished but the ability for ultraviolet ray shielding is not sufficient.

OBJECT OF THE INVENTION

The present invention is carried out concerning above mentioned circumstance, whose object is to provide metal oxide doped cerium oxides with strong ultraviolet ray shielding ability, lower catalytic activity and with excellent transparency. Further, the other object of this invention is to provide a composite composition of said metal oxide doped cerium oxides coated with metal oxide. Furthermore, the other object of this invention is to provide a resin composition or a cosmetic composition to which said metal oxide doped cerium oxides or a composite thereof is admixed with.

BRIEF SUMMARY OF THE INVENTION

That is, the present invention is the metal oxide doped cerium oxides composed of cerium oxide in which metal ion having larger ion radius than that of tetravalent cerium ion ($Ce^{4+}$) and/or lower valence metal ion than $Ce^{4+}$ are doped. As the concrete example of a metal ion used in this doping, $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$, $Ce^{3+}$ and the like can be mentioned. The desirable cerium oxide concentration in said metal oxide solid doped cerium oxide is 40 to 98 molar %. Further, when the color index of said metal oxide doped cerium oxide is estimated by L*, a* and b* space, the desirable region of L* is larger than 80, the desirable region of a* is smaller than 4 by absolute value and desirable region of b* is smaller than 10 by absolute value, further the desirable average particle size is ultra fine particle of 2 to 4 nm.

Further the metal oxide doped cerium oxides of this invention can be prepared by following steps. That is, prepare the metal oxide doped cerium oxide at the temperature lower than 60° C. and in the condition of pH higher than 5 by reacting aqueous solution of cerium salt, aqueous solution of metal ion having larger ion radius than that of $Ce^{4+}$ and/or lower valence metal ion than $Ce^{4+}$ and alkali, then by adding oxidizing agent in it at the temperature lower than 60° C. Furthermore the metal oxide doped cerium oxide of this invention can be prepared by adding and mixing aqueous solution of cerium salt, aqueous solution of metal ion having larger ion radius than that of $Ce^{4+}$ and/or lower valence metal ion than $Ce^{4+}$, alkali and oxidizing agent simultaneously at the temperature lower than 60° C. and in the condition of pH higher than 5.

The present invention also relates to a composite composition of said metal oxide doped cerium oxides coated by one or more kinds of oxide selected from the group composed of silicon oxide, zirconium oxide, aluminium oxide, iron oxide and titanium dioxide. Further, the present invention relates to the resin composition to which said metal oxide doped cerium oxide or the composite composition thereof is blended. Still further, the present invention relates to the cosmetic composition to which said metal oxide doped cerium oxide or the composite composition thereof is blended. The surface treated metal oxide doped cerium oxides or the composite composition thereof can be blended to the cosmetic composition. And, said cosmetic composition can contain an ultraviolet ray absorbing agent, and/or an ultraviolet ray scattering agent. As the desirable example of said ultraviolet ray absorbing agent, one or more kinds of compound selected from the group composed of oxybenzone, octyl metoxycinnamate and 4tertbutyl-4'-methoxy dibenzoylmethane can be mentioned, and the desirable contents of the ultraviolet ray absorbing agent is 0.1 to 40% by weight. As the desirable example of said ultraviolet ray scattering agent, titanium dioxide and/or zinc oxide can be mentioned, and the desirable contents of the ultraviolet ray scattering agent is 0.1 to 50% by weight. Above mentioned cosmetic composition is suited to be used as a sunscreen cosmetic composition.

The metal oxide doped cerium oxide of this invention is the cerium oxide in which metal ion having larger ion radius than that of $Ce^{4+}$ and/or lower valence metal ion than $Ce^{4+}$ are doped. By doping said metal ion, the catalytic activity of cerium oxide can be reduced Further, by doping said metal ion, the transparency of cerium oxide is improved and the ultraviolet ray shielding effect can be improved. As the concrete example of metal ion which has larger ion radius than $Ce^{4+}$ (ion radius of $Ce^{4+}$ is 0.097 nm), $Ca^{2+}$, $La^{3+}$, $Nd^{3+}$, $Eu^{3+}$, $Tb^{3+}$, $Sm^{3+}$, and $Ce^{3+}$ can be mentioned. As the concrete example of metal ion which has lower valence than $Ce^{4+}$, $Y^{3+}$, $Mg^{2+}$, $Sr^{2+}$ and $Ba^{2+}$ can be mentioned besides above mentioned metal ions. These metal ions can be used alone or together with. In addition, the desirable concentration of metal oxide doped cerium oxide is 40 to 98 molar %.

The metal oxide doped cerium oxide of this invention can be prepared by following steps. That is, prepare metal hydroxide doped cerium hydroxide, for example, at the temperature lower than 60° C. and in the condition of pH higher than 5, by reacting aqueous solution of cerium salt, aqueous solution of metal ion having larger ion radius than that of $Ce^{4+}$ and/or lower valence metal ion than $Ce^{4+}$ and alkali, then add oxidizing agent in it maintaining the temperature lower than 60° C. The obtained reacted product is rinsed by water, filtered, and dried or calcined then pulverized. Thus the metal oxide doped cerium oxide can be obtained. As the concrete example for the preparation of said solid solution of cerium hydroxide and metal hydroxide following methods can be mentioned. That is, (1) the method to add aqueous solution of cerium salt and aqueous solution of salt of metal to be solid solved simultaneously into a container in which alkaline solution is contained, or (2) the method to add aqueous solution of cerium salt, alkaline solution and aqueous solution of salt of metal to be solid solved simultaneously into a container in which water is contained.

Furthermore the metal oxide doped cerium oxide of this invention can be prepared by adding and mixing aqueous solution of cerium salt, aqueous solution of metal ion having larger ion radius than that of $Ce^{4+}$ and/or lower valence metal ion than $Ce^{4+}$, alkali and oxidizing agent simultaneously. For instance, at the temperature lower than 60° C. and in the condition of pH higher than 5, aqueous solution of cerium salt, aqueous solution of salt of metal to be solid solved, alkaline solution and hydrogen peroxide which is an oxidizing agent are added simultaneously into a container in which water is contained. The obtained reacted product, is rinsed by water and filtered, dried or calcined then pulverized, thus the fine particles of metal oxide doped cerium oxide can be prepared.

Aqueous solution of cerium salt which is used in above mentioned reaction, can be prepared by solving e.g. cerium carbonate in aqueous solution of hydrochloric acid or nitric acid, or by solving cerium chloride, cerium nitrate, cerium sulfate or cerium acetate in water. As alkali, aqueous solution of alkali metal hydroxide such as sodium hydroxide or potassium hydroxide, or aqueous solution of ammonia can be used. Further, as the salt of metal to be doped, for example, chloride, salt, of nitric acid, salt of sulfuric acid or salt of acetic acid can be mentioned. As the oxidizing agent, hydrogen peroxide, hypochlorous acid, sodium hypoclilorite, potassium hypochlorite, calcium hypochlorite and ozone can be used. In above mentioned methods, the doping is carried out in aqueous solution, however not limited with these examples.

In any kind of above mentioned reacting method, nano-size particles of metal oxide doped cerium oxide having 2–4 nm average diameter can be obtained by keeping the temperature of solution lower than 60° C., desirably lower than 40° C. and by rising pH higher than 5 during the adding process of oxidizing agent. Such kind of fine pulverized particles of metal oxide doped cerium oxide have a superior transparency at visible ray range and have an excellent dispersability, further, have a good ultraviolet ray shielding effect.

Further, in any kind of above mentioned reacting method, the yellowish tendency of metal oxide doped cerium oxide can be moderated and the white particles are obtained. And when the color index is estimated by L*, a* and b* space, the metal oxide doped cerium oxide whose L* is larger than 80, a* is smaller than 4 by absolute value and b* is smaller than 10 by absolute value can be obtained. In this invention, the term of L*, a* and b* space is regulated by CIE1976L* a* b* color space which is authorized by CIE (Commission Internationale de Enluminure) on 1976. This color space is a coordinate having axis of L*, a* and b* which are regulated by following numerical formulae.

$$L^* = 116(Y/Y_0)^{1/3} - 16$$

$$a^* = 500[(X/X_0)^{1/3} - (Y/Y_0)^{1/3}]$$

$$b^* = 200[(Y/Y_0)^{1/3} - (Z/Z_0)^{1/3}]$$

(wherein, $X/X_0$, $Y/Y_0$, $Z/Z_0 > 0.008856$, X,Y and Z indicate 3 stimulate values of object color, $X_0$, $Y_0$ and $Z_0$ indicate 3 stimulate values of color source which illuminates the object, and standardized to $Y_0 = 100$).

In the present invention, color index estimated by L*, a* and b* space is settled to $L^* \geq 80$, $|a^*| \leq 4$, $|b^*| \leq 10$. And each L*, a* and b* value are measured by color difference meter (product of Nihon Denshoku Kogyo).

Said metal oxide doped cerium oxide of this invention can be used as the composite form, namely coated with oxide (hereinafter said composite can be expressed as "oxide coated metal oxide doped cerium oxide"). As the oxide to be used for the preparation of said oxide coated metal oxide doped cerium oxide, one or more kinds of compound selected from the group composed of silicon oxide, zirconium oxide, aluminum oxide, iron oxide and titanium dioxide. By the use of composite of metal oxide doped cerium oxide which is coated with oxide, the catalytic activity can be more weakened and the dispersability can be improved.

The oxide coated metal oxide doped cerium oxide can be prepared by the further treatment of metal oxide doped cerium oxide prepared by the use of afore mentioned starting materials and by afore mentioned method with said oxide. For example, aqueous solution of cerium salt, aqueous solution of salt of metal to be doped (e.g. salt of calcium) and aqueous solution of alkali are added into water which is kept at the temperature lower than 60° C. and higher than pH 9, then calcium hydroxide doped cerium hydroxide can be obtained. An oxidizing agent such as hydrogen peroxide is further added to generate calcium oxide doped cerium oxide. Then heated to the temperature higher than 80° C. and keeping pH higher than 9, aqueous solution of sodium silicate and aqueous solution of mineral acid such as hydrochloric acid, nitric acid or sulfuric acid are added to coat silicon oxide over calcium oxide doped cerium oxide, and rinsed by water, filtrated, dried, calcined and pulverized. Thus the silicon oxide coated calcium oxide doped cerium oxide can be obtained. In this case, desirable amount, of sodium silicate to be added is 2 to 60% by weight, to coat subject of solid solution as $SiO_2$. Also in this case, by keeping pH of solution under 8 at the finishing point of oxidation, the yellowish tendency of oxide coated metal oxide doped cerium oxide can be weakened and improve the color index, and the metal oxide doped cerium oxide whose L* value is bigger than 80, absolute value of a* is smaller than 4 and absolute value of b* is smaller than 10 when color index is estimated by L* a* and b* space can be obtained. Further, by keeping pH of solution higher than 5 during oxidizing agent adding process, ultra fine particles of silicon oxide coated calcium oxide doped cerium oxide whose average particle diameter is 2 to 4 nm can be obtained.

BRIEF ILLUSTRATION OF THE DRAWING

DETAILED DESCRIPTION OF THE INVENTION

Figure 1:
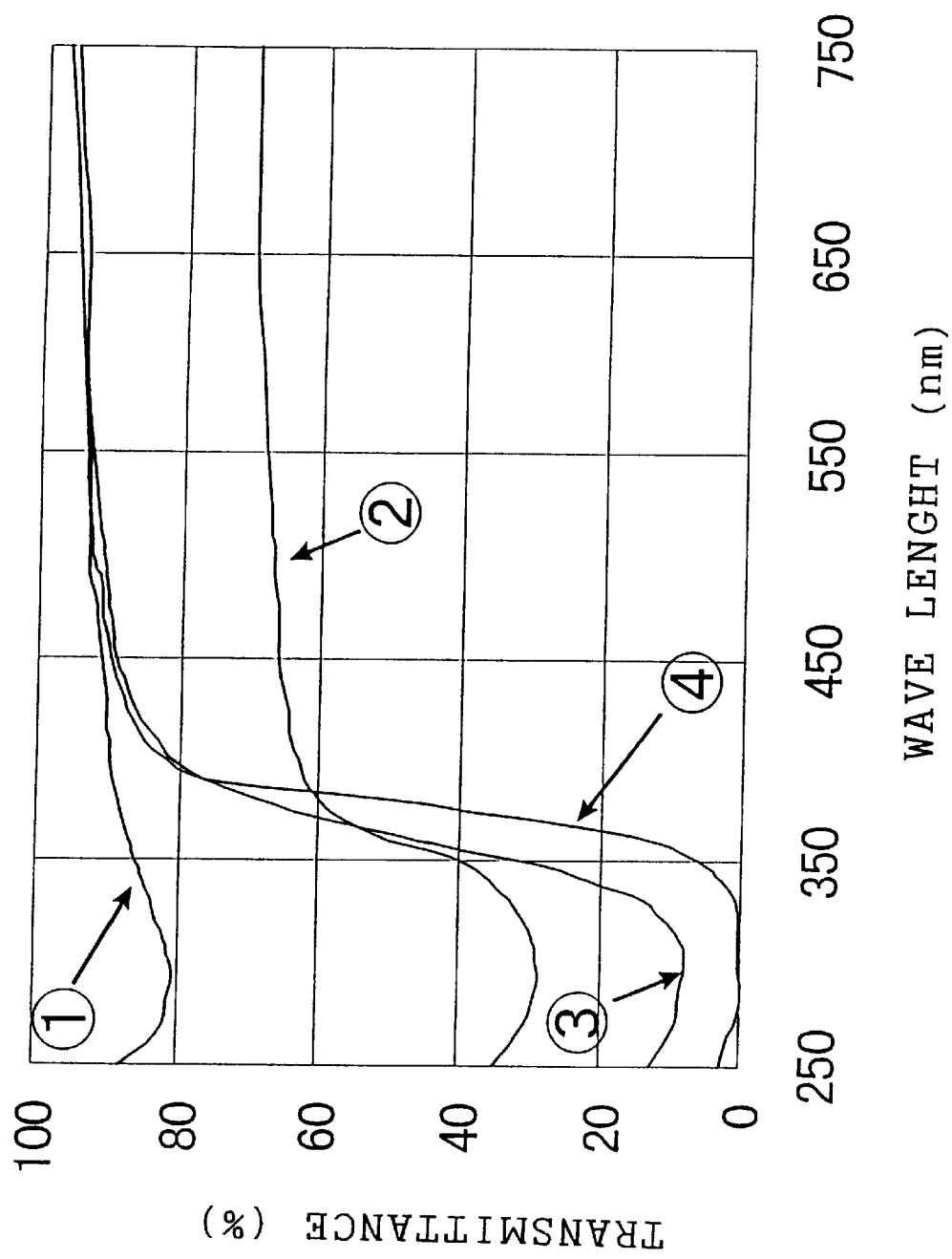
FIG. 1 is the graph which shows the light transmittance of the metal oxide doped cerium oxide of this invention.

The metal oxide doped cerium oxide of this invention has an excellent ultraviolet ray shielding effect. FIG. 1 shows the results of measurement, of the light transmittance as a function of wavelength of the metal oxide doped cerium oxide obtained by above mentioned method. The light transmittance is measured according to the following method. That is, each specimen is added to and dispersed in 6 ml of clear lacquer in such an amount that the content thereof is 3.0% by weight by using a Hoover muller (rotating at 50 revolutions×2) and mixed. The obtained solution is coated on a transparent quartz board by 30 μm thickness and the light transmittance is measured by a spectrophtometer (UV-2200, product of Shimadzu Seisakusho Co., Ltd.).

In FIG. 1, specimen (1) contains no additives, specimen (2) is high purity pulverized cerium oxide particles (average particle size is 10 μm) on market, specimen (3) is europium oxide doped cerium oxide of this invention whose molar ratio of $Ce^{4+}$ and $Eu^{3+}$ is 7:3, and specimen (4) is calcium oxide doped cerium oxide of this invention whose molar ratio $Ce^{4+}$ and $Ca^{2+}$ is 8:2.

As clearly understood from FIG. 1, europium oxide doped cerium oxide particles (3) and calcium oxide doped cerium oxide particles (4) of this invention are superior to high purity cerium oxide particles (2) on market at the ultraviolet ray shielding effect in the wavelength range of 250 to 400 nm, further at the transparency in the visible wavelength of 400 to 800 nm.

Figure 2:
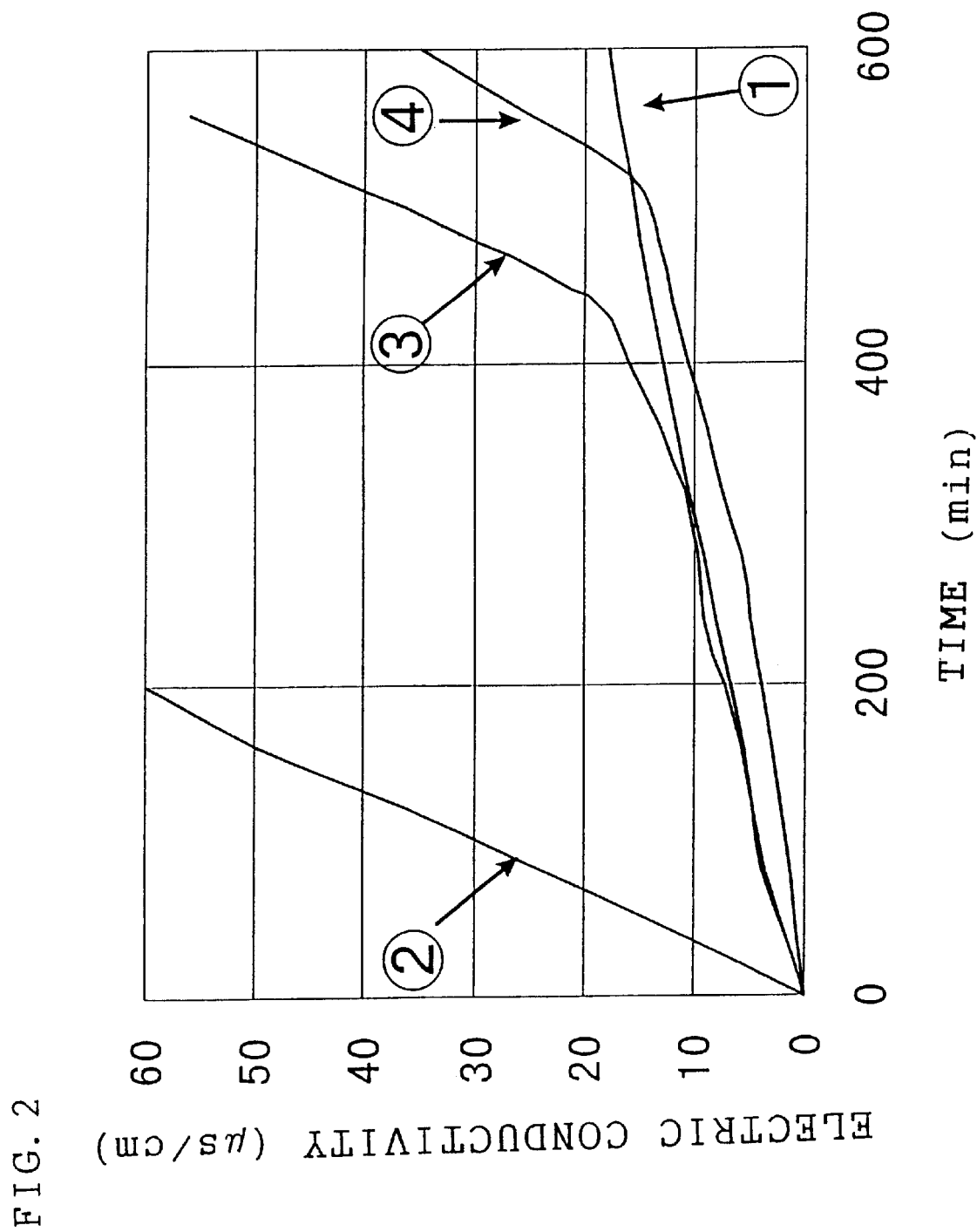
FIG. 2 is the graph which shows the catalytic activity of the metal oxide doped cerium oxide of this invention.

FIG. 2 shows the estimation results of catalytic activity of metal oxide doped cerium oxide obtained by above mentioned method measured by RANSHIMAT method which is a kind of CDM (Contactometric Determination Method). As the CDM apparatus, Model E679 (product of Metrom Co.) is used. 0.5 g of specimen and 5 g of caster oil (product of Ito Seiyu Co.) are mixed together, poured into a sealed container placed in a thermostat set up to 130° C. for 10 hours. Air is introduced with bubbling by 20 liter/hour flow rate to the caster oil. Air of head space is introduced to the water contained in a separated flask, and the change of electro conductivity of trapped water caused by volatile decomposition of caster oil is detected by measuring cell. The degree of change of electric conductivity by lapse of time is regarded as the intensity of catalytic activity. The same specimen used at the measurement of light transmittance is used.

As clearly understood from FIG. 2, the europium oxide doped cerium oxide particles (3) and the calcium oxide doped cerium oxide particles (4) of this invention have smaller tendency to promote the oxidation and decomposition of caster oil compared with the high purity cerium oxide particles (2) on market, and it is obvious that; the catalytic activity of (2) and (3) is remarkably reduced.

A resin composition and a cosmetic composition of this invention are illustrated as follows. In general, a resin composition degrades by the absorption of ultraviolet ray of sun light. As the countermeasure method against the degradation by ultraviolet ray, the metal oxide doped cerium oxide is blended to the resin composition. Thus, the resistance to light is improved and the decomposition by light can be prevented or reduced. Further, the light decomposition of the contents which is covered by a transparent resin composition by ultraviolet ray can be prevented or reduced. When the catalytic activity of metal oxide doped cerium oxide of this invention is compared with that of cerium oxide, it is remarkably weaker, therefore, the oxidizing decomposition of resin composition caused by cerium oxide can be reduced. The resin composition of this invention indicates a molded product of synthetic resin such as polyvinylchloride, polypropylene, polyethylene, polyamide, polyester or polycarbonate, or natural resin, or a coating in which said resins are blended.

A cosmetic composition of this invention is illustrated as follows. The cosmetic composition of this invention exhibits excellent transparency and high sunscreening effect by virtue of the inventive metal oxide doped cerium oxide particles containing therein. Because the catalytic activity of the metal oxide doped cerium oxide of this invention is remarkably weaker than that of cerium oxide, the decomposition of blended component in cosmetic compound such as oil caused by cerium oxide can be reduced. As a concrete example of the formulation type of the inventive cosmetic composition, a skin care cosmetic composition such as milk lotion, skin lotion and the like, a make up cosmetic composition such as foundation or lipstick and a hair care cosmetic composition can be mentioned, desirably a sunscreening cosmetic composition can be mentioned. The amount of the metal oxide doped cerium oxide to be blended in a cosmetic composition is not limited, however, the desirable amount is 1 to 70% by weight.

It is optional that the metal oxide doped cerium oxide or an oxide coated metal oxide doped cerium oxide composite particles are subjected to a surface treatment before being incorporated in a cosmetic composition. As the concrete example for the surface treatment method, a treatment by ordinary type oil and fat, a metal soap, silicone, dialkyl phosphoric acid, perfluoroalkyl group containing compound, amino acid, lecithin or collagen, can be mentioned.

The sunscreening effect exhibited by the inventive cosmetic composition can be further enhanced by containing the composition with other well known ultraviolet ray absorbers and/or ultraviolet ray scattering agents in combination with the metal oxide doped cerium oxide particles. The ultraviolet ray absorbing agent suitable for the purpose includes oxybenzone, octyl methoxycinnamate, 4-tert-butyl-4'-metahoxydibenzoylmethane and the like either singly or as a combination of two kinds or more according to need. The containing amount thereof is, though not particularly limitative, usually in the range from 0.1 to 40% by weight of the composition. The ultraviolet ray scattering agent used for the above mentioned purpose is preferably a fine powder of titanium dioxide or zinc oxide, more preferably, having an average particle diameter not exceeding 0.05 $\mu$m. The containing amount thereof is desirably in the range from 0.1 to 50% by weight.

Any conventional cosmetic ingredients can be used together with the cosmetic compositions. Typical examples of such ingredients are cosmetic powder, surface active agents, oil, polymeric compounds, aesthetic ingredients, moisturizing agents, coloring agents, preservatives, perfumery and so on each in a limited amount not to decrease the advantages obtained by the invention.

The effect of this invention is illustrated as follows. The catalytic activity of metal oxide doped cerium oxide of this invention is reduced by doping metal oxide in cerium oxide, the transparency in the visible range is good and the effect to shield the ultraviolet ray at A-range and the ultraviolet ray at B-range is increased. And, the resin composition or the cosmetic composition in which said metal oxide doped cerium oxide particles are blended have an excellent transparency and ultraviolet ray shielding effect. A resin or a cosmetic in which conventional cerium oxide is blended has a tendency that the contained oil or blended components are easily oxidized and decomposed by the catalytic activity of contained cerium oxide, on the contrary, since the catalytic activity of metal oxide doped cerium oxide of this invention is reduced, said defect can not be observed and has an excellent stability for aging. A complex of metal oxide doped cerium oxide whose surface is coated with oxide, can further reduce and weaken the catalytic activity and can improve the dispersability.

EXAMPLES

The present invention will be understood more readily with reference to the Example and the Comparative Examples, however, these are only intended to illustrate the invention and not be construed to limit the scope of the invention.

Example 1

Europium Oxide Doped Cerium Oxide Particles 342 g of cerium chloride ($CeCl_3$) is dissolved in water and 3 liter of cerium chloride aqueous solution is prepared. 155 g of europium chloride ($EuCl_3$) is dissolved in water and 3 liter of europium chloride aqueous solution is prepared. Further 237 g of sodium hydroxide (NaOH) is dissolved in water and 12 liter of sodium hydroxide aqueous solution is prepared. Furthermore, 118 g of 30 wt % hydrogen peroxide is dissolved in water and 3 liter of hydrogen peroxide aqueous solution is prepared. 12 liter of sodium hydroxide aqueous solution is heated to 30–40° C. and said cerium chloride aqueous solution and europium chloride aqueous solution are added simultaneously by constant stirring maintaining pH of reacting solution higher than 11 and temperature of the solution lower than 40° C. After adding continue the stirring for 30 minutes, maintain the temperature of reacting solution at 60° C., then aqueous solution of hydrogen peroxide is added. After the adding, continue the constant stirring for 30. minutes, then the reacted product is rinsed by water, filtered and dried, thus the europium oxide doped cerium oxide particles whose molar ratio of $Ce^{4+}$ and $Eu^{3+}$ is 7:3 is obtained.

Example 2

White Colored Calcium Oxide Doped Cerium Oxide Particles 390 g of cerium chloride ($CeCl_3$) is dissolved in water and 3 liter of cerium chloride aqueous solution is prepared. 45 g of calcium chloride ($CaCl_2$) is dissolved in water and 3 liter of aqueous solution of calcium chloride is prepared. Further 237 g of sodium hydroxide (NaOH) is dissolved in water and 8 liter of sodium hydroxide aqueous solution is prepared. Furthermore, 118 g of 30 wt % hydrogen peroxide is dissolved in water and 3 liter of hydrogen peroxide aqueous solution is prepared. To 8 liter of water heated to 30–40° C., said cerium chloride aqueous solution, calcium chloride aqueous solution and sodium hydroxide aqueous solution are added simultaneously by constant siring maintaining pH of reacting solution 9–11 and temperature of the solution lower than 40° C. After the reaction, add hydrochloric acid so as to adjust pH of reacting solution to 5–7 and the temperature of solution to 60° C., the aqueous solution of hydrogen peroxide is added. The reacted product is rinsed by water, filtered and dried, thus the calcium oxide doped cerium oxide particles whose molar ratio of $Ce^{4+}$ and $Ca^{2+}$ is 8:2 is obtained.

The color index of obtained solid solution is L* value; 94.0, a* value; -1.6 and b* value; 6.2.

20 g of obtained powder is press molded on pan of 6 cm and L*, a* and b* values are measured by a color difference meter (product of Nihon Denshoku Kogyo).

Example 3

Ultra Fine Particles of Calcium Oxide Doped Cerium Oxide 390 g of cerium chloride ($CeCl_3$) is dissolved in water and 3 liter of cerium chloride aqueous solution is prepared. 45 g of calcium chloride ($CaCl_2$) is dissolved in water and 3 liter of aqueous solution of calcium chloride is prepared. Further 237 g of sodium hydroxide (NaOH) is dissolved in water and 3 liter of sodium hydroxide aqueous solution is prepared. Furthermore, 118 g of 30 wt % hydrogen peroxide is dissolved in water and 3 liter of hydrogen peroxide aqueous solution is prepared. To 8 liter of water heated to 30–40° C., said cerium chloride aqueous solution, calcium chloride aqueous solution and sodium hydroxide aqueous solution are added simultaneously by constant stirring maintaining pH of reacting solution 9–11 and temperature of the solution lower than 40° C. After the reaction, the reacted product is rinsed by water, filtrated and dried, thus the calcium oxide doped cerium oxide whose molar ratio of $Ce^{4+}$ and $Ca^{2+}$ is 8:2 is obtained.

The average particle diameter of metal oxide is 2.8 nm. The diameter of particle is measured by a transmission electron microscope (product of JEOL Co., Ltd.). Namely, diameter of 100 particles are measured by naked eyes of inspector and averaged.

Example 4

Composite of Silicon Oxide Coated Calcium Oxide Doped Cerium Oxide 562 g of sodium silicate solution (content of $SiO_2$ is 28.5 wt %) is dissolved in water and 2 liter of sodium silicate solution is prepared. 75.8 g of 95 wt % sulfuric acid is diluted with water and 2 liter of diluted sulfuric acid is prepared. The aqueous solution containing calcium oxide doped cerium oxide obtained in Example 2 is heated to the temperature higher than 80° C. with constant stirring, aqueous solution of sodium silicate and diluted sulfuric acid are added simultaneously as to maintain pH of reacting solution higher than 9. After the adding of both solution, the solution is continued to stir for another 30 minutes and adjusted pH of reacting solution to 7–8 by adding diluted sulfuric acid. The reacted product is rinsed by water, filtered, dried and pulverized, thus the 30 wt % $SiO_2$ coated calcium oxide doped cerium oxide (silicon oxide coated calcium oxide doped cerium oxide) is obtained.

Example 5

Figure 3:
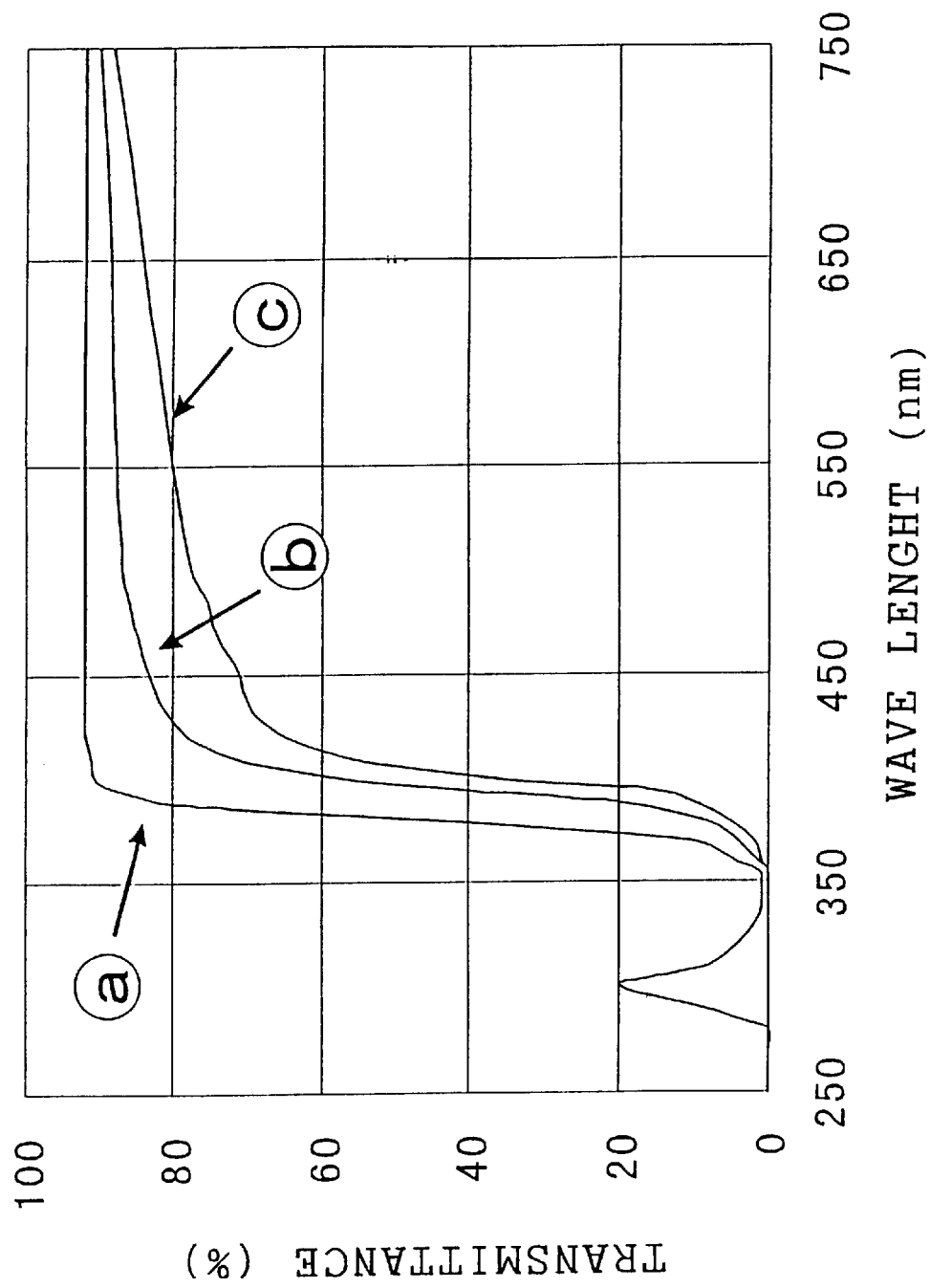
FIG. 3 is the graph which shows the light transmittance of the soft polyvinyl chloride sheet containing the metal oxide doped cerium oxide of this invention.

0.05 and 1 wt % of the white calcium oxide doped cerium oxide particles obtained in Example 2 are blended to plasticized polyvinyl chloride resin. The polyvinyl chloride resin without doped particles and the two resin composition blended with said both amounts of particles are each shaped into a sheet having a thickness of 0.24 mm by using hot calendering rollers. Each of thus prepared sheets are subjected to the measurement of the transmittance on a spectrophotometer (UV-2200, product of Shimadziu Seisakusho Co., Ltd.). Results illustrated in FIG. 3 are obtained.
Specimen a is a sheet with no additives,
Specimen b is a sheet containing 0.5 wt. % of calcium oxide doped cerium oxide.
Specimen c is a sheet containing 1.0 wt % of calcium oxide doped cerium oxide.

It is clearly understood from FIG. 3, that the calcium oxide doped cerium oxide of this invention can improve the shielding effect in the range of ultraviolet ray by the higher blending ratio, however it maintains good transparency in the range of visible ray.

Example 6

Four kinds of cream foundation of following recipe are prepared containing metal oxide doped cerium oxide or composite of silicon oxide coated calcium oxide doped cerium oxide obtained from Example 1 to Example 4.
Recipe

|  |  | wt % |
|---|---|---|
| (1) | stearic acid | 5.0 |
| (2) | oleophilic glyceryl monostearate | 2.5 |
| (3) | cetanol | 1.5 |
| (4) | isopropylene glycol monolaurate | 2.5 |
| (5) | liquid parafin | 8.0 |
| (6) | isopropyl myristate | 7.0 |
| (7) | propyl paraben | 0.1 |
| (8) | purified water | 47.3 |
| (9) | triethanolamine | 1.2 |
| (10) | sorbitol | 3.0 |
| (11) | methyl paraben | 0.2 |
| (12) | titanium dioxide | 8.0 |
| (13) | kaolin | 5.0 |
| (14) | doped particles obtained from Example 1, 2, 3 or 4 | 3.0 |
| (15) | bentonite | 1.0 |
| (16) | red iron oxide | 2.5 |
| (17) | yellow iron oxide | 2.0 |
| (18) | black iron oxide | 0.2 |

Method for Preparation
(a) Ingredients (12) to (14) and (16) to (18) are blended together.

(b) Ingredient (15) is admixed with (8) heated at 80° C. to effect full swelling, then ingredients (9) to (11) are added and dissolved therein. To the mixture, the prepared mixture (a) is added and dissolved at 80° C. (water phase).
(c) Ingredients (1) to (7) are mixed together and dissolved at 80° C. (oily phase).
(d) To the prepared (water phase), the prepared (oily phase) is added and emulsified. After that, cooled down to 35° C. under constant stirring.

The cream foundations obtained as above, exhibit excellent transparency of coated layer along with good spreadability and an excellent sunscreening effect.

Example 7

150 g of the ultra fine particles of calcium oxide doped cerium oxide obtained in Example 3 and 200 g of purified water are taken into a flask and are mixed together with heating to 70° C. to prepare an aqueous slurry. Further, an aqueous emulsion obtained from 6 g of diethanolamine salt of perfluoroalkyl phosphoric acid ester (Asahiguard AG 530, a product of Asahi Glass Co., Ltd.) and 150 g of purified water are admixed and emulsified. The obtained emulsion is added gradually into said slurry and followed by continuous stirring for 1 hour. After acidification, the aqueous dispersion is rinsed with water, filtered, dried then 154 g of fluorinated calcium oxide doped cerium oxide fine particles are obtained (hereinafter shortened to fluorinated doped particle).

Example 8

150 g of the white calcium oxide doped cerium oxide obtained in Example 2 and 200 g of isopropanol are taken into a flask and are mixed together with heating to 70° C. to prepare an aqueous slurry, then 3 g of methyl hydrogen polysiloxan (product of Shin-Etsu Chemical Co., Ltd.) is added and mixed for 1 hour. And followed by removal of isopropyl alcohol by heating and vacuuming to give 152 g of silicone treated white calcium oxide doped cerium oxide (hereinafter, shortened to silicone treated doped particle).

Example 9

A sunscreen milk lotion is prepared by using fluorinated doped particles obtained in Example 7 according to the following recipe and preparing method.
Recipe

|  |  | wt % |
|---|---|---|
| (1) | fluorinated doped particles | 10.0 |
| (2) | microcrystalline wax | 1.0 |
| (3) | beeswax | 2.0 |
| (4) | squalane | 10.0 |
| (5) | dimethicone (10 cSt) | 10.0 |
| (6) | decamethyl cyclopentasiloxane | 10.0 |
| (7) | sorbitan sesquioleate | 4.0 |
| (8) | polyoxyethylene-methylpolysiloxane copolymer | 1.0 |
| (9) | oxybenzone | 0.1 |
| (10) | 1,3-buthyleneglycol | 9.0 |
| (11) | preservative | q.s. |
| (12) | purified water | balance |
| (13) | perfume | q.s. |

Method for Preparation
(a) Ingredients (2) to (9) are melted together by heat, and ingredient (1) is added and heated to 70° C.
(b) Ingredients (10) to (12) are mixed together by heating up to 70° C., and obtained mixture is added to (a) and emulsified.

(c) After (b) is cooled clown, ingredient (13) is added and mixed, thus the sunscreen milk lotion is obtained.

Comparative Example 1

A sunscreen milk lotion is prepared by same recipe and same method to Example 9 except using a high purity cerium oxide particles (average particle size is 10 μm) on the market instead of ingredient (1).

When the sunscreen milk lotion of Comparative Example 1 is applied on human skin, it exhibits a pale-white color and white powderiness not to give a natural feeling of cosmetic finish. On the contrary, the sunscreen milk lotion of Example 9 which relates to this invention exhibits a transparent and good cosmetic finish along with an excellent sunscreen effect and preservability.

Example 10

A powder foundation is prepared by using silicone treated solid doped particles obtained in Example 8 according to the following recipe and preparing method.
Recipe

|  | wt % |
|---|---|
| (1) silicone treated talc | 20.0 |
| (2) silicone treated mica | balance |
| (3) silicone treated titanium dioxide | 12.0 |
| (4) silicone treated red iron oxide | 1.0 |
| (5) silicone treated yellow iron oxide | 3.0 |
| (6) silicone treated black iron oxide | 3.0 |
| (7) silicone treated doped particles | 20.0 |
| (8) silicone treated zinc oxide | 1.0 |
| (9) squalane | 5.0 |
| (10) glyceryl tri-2-ethylhexanoate | 2.0 |
| (11) white vaseline | 1.0 |
| (12) preservative | q.s. |
| (13) perfume | q.s. |

Method for Preparation
(a) Ingredients (1) to (8) are blended together by a Henschel mixer.
(b) Ingredients (9) to (11) are heated and blended together and ingredients (12) and (13) are added.
(c) The obtained mixture in (b) is pulverized into a powder, molded by pressing and a powder foundation is obtained.

Comparative Example 2

A powder foundation is prepared by same recipe and same method to Example 10 except using a high purity cerium oxide particles (average particle size is 10 μm) on the market instead of ingredient (7).

When the powder foundation of Comparative Example 2 is applied on human skin, it exhibits a pale-white color and white powderiness not to give a natural feeling of cosmetic finish. On the contrary, the powder foundation of Example 10 which relates to this invention exhibits a transparent and good cosmetic finish along with an excellent sunscreen effect and preservability.

Example 11

A lipstick is prepared by using fine particles of calcium oxide doped cerium oxide obtained in Example 3 according to the following recipe and preparing method.
Recipe

|  | wt % |
|---|---|
| (1) ethylene-propylene copolymer | 9.0 |
| (2) microcrystalline wax | 5.0 |
| (3) candelilla wax | 3.0 |
| (4) ceresin wax | 3.0 |
| (5) lanolin | 10.0 |
| (6) caster oil | 20.0 |
| (7) hexyldecyl 2-ethylhexanoate | 26.9 |
| (8) D & C Red No. 6 | 2.0 |
| (9) D & C Red No. 7 | 1.0 |
| (10) D & C Orange No. 5 | 0.1 |
| (11) fine particles of calcium oxide doped cerium oxide | 20.0 |

Method for Preparation
(a) Ingredients (8) to (11) are blended together and added to a part of ingredient (6), then are mixed and dispersed by a mixing roller.
(b) Ingredients (1) to (5), remaining part of the ingredient (6) and (7) are heated and blended together, then prepared (a) is added and further mixed homogeneously.
(c) A container for lipstick is filled with the molten mixture of (b) and cooled clown rapidly, thus a lipstick is obtained.

Comparative Example 3

A powder foundation is prepared by same recipe and same method to Example 11 except using a fine particles of titanium dioxide instead of ingredient (11).

When the lipstick of Comparative Example 3 is applied on human lips, it exhibits a pale-white color and not give a natural and healthy feeling on lip. On the contrary, the lip stick of Example 11 which relates to this invention exhibits a transparent with healthy coloration along with an excellent sunscreen effect, and preservability.

Example 12

A pressed powder is prepared by using europium oxide doped cerium oxide obtained in Example 1 according to the following recipe and preparing method.
Recipe

|  | wt % |
|---|---|
| (1) europium oxide doped cerium oxide | 50.0 |
| (2) talc | 30.0 |
| (3) sericite | 6.0 |
| (4) kaolin | balance |
| (5) titanium dioxide | 3.0 |
| (6) zinc myristate | 2.0 |
| (7) red iron oxide | 0.2 |
| (8) yellow iron oxide | 0.8 |
| (9) squalane | 2.0 |
| (10) octyl methoxycinnamate | 2.0 |
| (11) preservative | q.s. |
| (12) perfume | q.s. |

Method for Preparation
(a) Ingredients (1) to (8) are blended together.
(b) Ingredients (9) to (12) are blended together and added to (a) and mixed homogeneously.
(c) The obtained mixture (b) is pulverized into a powder, molded by pressing and a pressed powder is obtained.

Comparative Example 4

A pressed powder is prepared by same recipe and same method to Example 12 except using fine particles of titanium dioxide instead of ingredient (1).

When the pressed powder of Comparative Example 4 is applied on human skin, it exhibits a pale-white color and white powderiness not to give a natural feeling of cosmetic finish. On the contrary, the pressed powder of Example 12 which relates to this invention exhibits a transparent and good cosmetic finish along with an excellent sunscreen effect and preservability.

What is claimed is:

1. An ultraviolet ray shielding agent of a metal ion doped cerium oxide comprising cerium oxide doped with a metal ion having a larger ion radius than that of tetravalent cerium ion and/or a lower valence metal ion than tetravalent cerium ion said metal ion doped cerium oxide being coated by one or more kinds of oxide selected from the group consisting of silicon oxide, zirconium oxide, aluminum oxide, iron oxide and titanium oxide.

2. A resin composition containing the ultraviolet ray shielding agent of claim 1.

3. A cosmetic composition containing the ultraviolet ray shielding agent of claim 1.

4. The cosmetic composition of claim 3, further comprising an ultraviolet ray absorbing agent and/or an ultraviolet ray scattering agent.

5. The cosmetic composition of claim 4, wherein the ultraviolet ray absorbing agent comprises at least one compound selected from the group consisting of oxybenzone, octyl metoxycinnamate and 4-tert-butyl-4'-methoxy dibenzoylmethane.

6. The cosmetic composition of claim 4, wherein the content of the ultraviolet ray absorbing agent is 0.1 to 40 wt %.

7. The cosmetic composition of claim 4, wherein the ultraviolet ray scattering agent comprises titanium dioxide and/or zinc oxide.

8. The cosmetic composition of claim 4, wherein the content of the ultraviolet ray scattering agent is 0.1 to 50 wt %.

9. The cosmetic composition of claim 3, wherein the cosmetic composition is a sunscreening cosmetic composition.

10. The resin composition according to claim 2, wherein the resin is a synthetic resin selected from the group consisting of polyvinylchloride, polypropylene, polyethylene, polyamide, polyester and polycarbonate.

11. The resin composition according to claim 2, wherein, the cerium oxide is doped with at least one metal ion selected from the group consisting of $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$ and $Ce^{3+}$.

12. The ultraviolet ray shielding agent of claim 1, wherein, the cerium oxide is doped with at least one metal ion selected from the group consisting of $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$ and $Ce^{3+}$.

13. The ultraviolet ray shielding agent of claim 1, wherein the content of cerium oxide in the metal oxide doped cerium oxide is from 40 to 98 mole percent.

14. The ultraviolet ray shielding agent of claim 1, wherein said metal ion doped cerium oxide has a color index, determined by L*, a* and b*, wherein L* is bigger than 80, a* is smaller than 4 by absolute value and b* is smaller than 10 by absolute value.

15. The ultraviolet ray shielding agent of claim 1, wherein the metal ion doped cerium oxide is in the form of ultrafine particles having an average particle size of 2 to 4 nm.

16. The cosmetic composition according to claim 3, wherein, the cerium oxide is doped with at least one metal ion selected from the group consisting of $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$ and $Ce^{3+}$.

17. The cosmetic composition according to claim 3, wherein the content of the cerium oxide in the metal ion doped cerium oxide is from 40 to 98 molar %.

18. The cosmetic composition according to claim 3, wherein said metal ion doped cerium oxide has a color index, determined by L*, a* and b*, wherein L* is bigger than 80, a* is smaller than 4 by absolute value and b* is smaller than 10 by absolute value.

19. The cosmetic composition according to claim 1, wherein the metal ion doped cerium oxide is in the form of ultrafine particles whose average particle size is 2 to 4 nm.

20. An ultraviolet ray shielding agent of a metal ion doped cerium oxide comprising cerium oxide doped with a metal ion having larger ion radius than that of tetravalent cerium ion and lower valence metal ion than tetravalent cerium ion said metal ion doped cerium oxide being coated by at least one oxide selected from the group consisting of silicon oxide, zirconium oxide, aluminum oxide, iron oxide and titanium oxide.

21. The ultraviolet ray shielding agent of claim 20, wherein the cerium oxide doped is doped with at least one metal ion selected from the group consisting of $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$ and $Ce^{3+}$.

22. The ultraviolet ray shielding agent of claim 20, wherein the content of cerium oxide in the metal ion doped cerium oxide is 40 to 98 molar %.

23. The ultraviolet ray shielding agent of claim 20, having a color index, determined by L*, a* and b*, wherein L* is bigger than 80, a* is smaller than 4 by absolute value and b* is smaller than 10 by absolute value.

24. the ultraviolet ray shielding agent of claim 20, wherein the metal ion doped cerium oxide is in the form of ultrafine particles having a size of 2 to 4 nm.

25. A resin composition containing the ultraviolet ray shielding agent of claim 20.

26. A cosmetic composition containing the ultraviolet ray shielding agent of claim 20.

27. The cosmetic composition of claim 26, further comprising an ultraviolet ray absorbing agent and/or an ultraviolet ray scattering agent.

28. The cosmetic composition of claim 27, wherein the content of the ultraviolet ray absorbing agent is 0.1 to 40 wt %.

29. The cosmetic composition of claim 27, wherein the ultraviolet ray absorbing agent comprises at least one compound selected from the group consisting of oxybenzone, octylmetoxycinnamate and 4-tert-butyl-4'-methoxydibenzoylmethane.

30. The cosmetic composition of claim 27, wherein the ultraviolet ray scattering agent comprises titanium dioxide and/or zinc oxide.

31. The cosmetic composition of claim 27, wherein the content of the ultraviolet ray scattering agent is 0.1 to 50 wt %.

32. The cosmetic composition of claim 26, wherein the cosmetic composition is a sunscreening cosmetic composition.

* * * * *

UNITED STATES PATENT AND TRADEMARK OFFICE
CERTIFICATE OF CORRECTION

PATENT NO.    : 6,623,858 B1                                              Page 1 of 1
DATED         : September 23, 2003
INVENTOR(S)   : Sinryo Yabe et al.

It is certified that error appears in the above-identified patent and that said Letters Patent is hereby corrected as shown below:

<u>Title page,</u>
Item [73], change

"[73] Assignees: Kose Corporation, Tokyo (JP);
  Nippon Inorganic Colour & Chemical Co., Ltd., Tokyo (JP)" to -- [73] Assignees: Kose Corporation, Tokyo (JP);
  Nippon Denko Co., Ltd., Tokyo (JP) --

Signed and Sealed this

Twenty-seventh Day of April, 2004

JON W. DUDAS
*Acting Director of the United States Patent and Trademark Office*